United States Patent [19]

Tang et al.

[11] Patent Number: 4,590,008

[45] Date of Patent: May 20, 1986

[54] NOVEL ORGANIC PEROXYDICARBONATES

[75] Inventors: Robert H. Tang, Norton; John C. Crano, Akron, both of Ohio

[73] Assignee: PPG Industries, Inc., Pittsburgh, Pa.

[21] Appl. No.: 618,273

[22] Filed: Jun. 7, 1984

[51] Int. Cl.$^4$ ............................................. C07C 69/003
[52] U.S. Cl. .................................. 558/264; 526/230.5; 526/228
[58] Field of Search ................................... 260/453 RZ

[56] References Cited

U.S. PATENT DOCUMENTS

| Re. 25,763 | 4/1965 | Marous et al. | 526/228 |
|---|---|---|---|
| 2,370,588 | 2/1945 | Strain | 260/453 R |
| 2,843,576 | 7/1958 | Dunn et al. | 526/193 |
| 4,069,239 | 1/1978 | Lewis et al. | 260/453 RZ |
| 4,269,726 | 5/1981 | Kolczynski et al. | 260/453 RZ |
| 4,285,877 | 8/1981 | Halle et al. | 260/453 RZ |

OTHER PUBLICATIONS

Esters of Peroxycarbonic Acids, F. Strain et al, J. A. Chem. Soc. vol. 72, pp. 1254–1263 (1950).

Primary Examiner—John Kight
Assistant Examiner—Kriellion Morgan
Attorney, Agent, or Firm—Irwin M. Stein

[57] ABSTRACT

Organic peroxydicarbonates such as bis[3-(isobutyryloxy)-2,2,4-trimethylpentyl] peroxydicarbonate are described. The peroxydicarbonates are useful as initiators for the polymerization or copolymerization of vinyl acetate and may be used in combination with the more commonly used peroxydicarbonates such as diisopropyl peroxydicarbonate.

7 Claims, No Drawings

NOVEL ORGANIC PEROXYDICARBONATES

DESCRIPTION OF THE INVENTION

The present invention relates to certain novel peroxydicarbonates and to their use in the polymerization and copolymerization of ethylenically unsaturated monomers, such as vinyl chloride. The utility of certain peroxydicarbonate compounds for initiating polymerization reactions is known. See, for example, U.S. Pat. No. 2,370,588 and J. Am. Chem. Soc., 72, 1254 (1950) of Strain et al, which discloses generally the preparation of various dialkyl peroxydicarbonates and their use as polymerization initiators. See also, Dunn et al, U.S. Pat. No. 2,843,576 and Marous et al, U.S. Pat. No. Re. 25,763.

The physical properties of polyvinyl chloride prepared by emulsion polymerization of vinyl chloride monomer depend to a degree on the temperature and rate at which the monomer is polymerized. Thus, a change in one or both of such polymerization conditions will usually effect the physical properties of the resulting polymer. The temperatures at which an organic peroxide, such as the commercially available peroxydicarbonates, efficiently initiates and maintains the polymerization of ethylenically unsaturated monomers is an inherent property of the organic peroxide. Similarly, the half-life of an organic peroxide at any given temperature is also an inherent property. Hence, if a change in the polymerization rate at a given temperature or a change in the polymerization temperature is desired, such change may also require a change in the organic peroxide initiator used.

The polyvinyl chloride industry has been engaged in efforts to produce polymers at different polymerization conditions, thereby to produce products with varying physical properties. Thus, there is a continuing need for new organic peroxide initiators, such as the organic peroxydicarbonates, which will generate free radicals, efficiently at the various polymerization conditions chosen by that industry.

It has now been discovered that peroxydicarbonate compounds corresponding to the following graphic formulae I, II and III and mixtures of such compounds can be used to polymerize ethylenically unsaturated polymerizable materials such as vinyl chloride monomer.

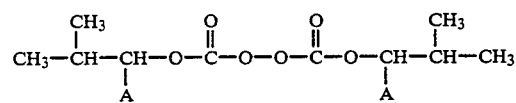

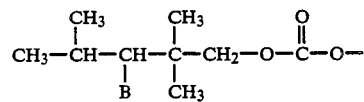

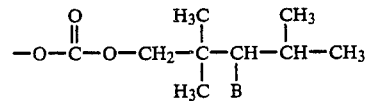

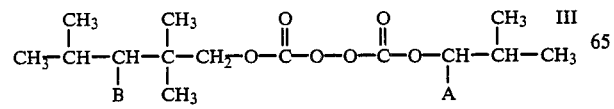

wherein A is the radical,

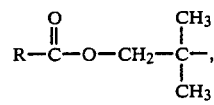

B is the radical,

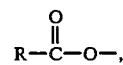

and R is a $C_1$-$C_7$, preferably a $C_1$-$C_5$, branched or straight chain alkyl radical.

Peroxydicarbonates of the present invention are liquid at room temperature, and are efficient at the polymerization temperatures at which the normally liquid commercially peroxydicarbonates are used. Further, it has been found surprisingly that the half-life of a mixture of the peroxydicarbonates of the present invention wherein R is isopropyl, e.g., the peroxydicarbonate mixture of Example II, has a half-life at 50° C. (measured in trichloroethylene) of about 12.1 hours as contrasted with 9.0 and 9.2 hours for di(secondary butyl)-peroxydicarbonate and di(2-ethylhexyl)peroxydicarbonate respectively.

The novel peroxydicarbonates of the present invention may be employed for the polymerization and copolymerization of ethylenically unsaturated monomers. Examples of such monomers include, but are not limited to, vinyl aromatic compounds such as styrene and p-chlorostyrene; esters of aliphatic alpha unsaturated monocarboxylic acids such as methylmethacrylate, n-butylacrylate, and ethylacrylate; vinyl esters such as vinyl acetate; vinyl halides such as vinyl chloride; vinyl ethers such as vinyl methyl ether; vinylidene halides such as vinylidene chloride; and alpha-ethylenically unsaturated hydrocarbons such as ethylene and propylene, as well as for the cross-linking of unsaturated polyester resins. The peroxydicarbonates of the present invention may also be used to polymerize monomers having allylic unsaturation, such as diethylene glycol bis(allyl carbonate). The polymerization of the aforesaid unsaturated monomers may be performed as a suspension, emulsion, solution or bulk polymerization.

DETAILED DESCRIPTION OF THE INVENTION

The present invention relates to novel organic peroxydicarbonates which can be represented by the following graphic formulae and to mixtures of such compounds.

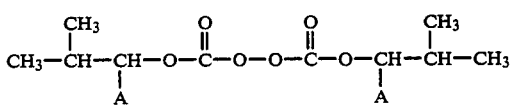

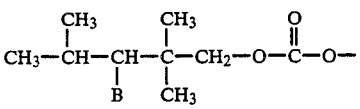

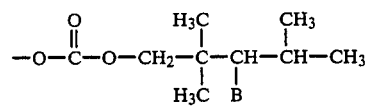

-continued

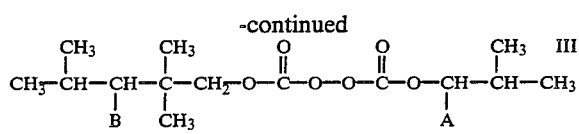

wherein A is the radical,

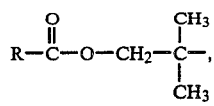

B is the radical,

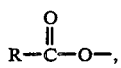

and R is a $C_1$–$C_7$, preferably a $C_1$–$C_5$, branched or straight chain alkyl radical. Examples of radicals from which R can be selected include: methyl, ethyl, n-propyl, isopropyl, n-butyl, secondary butyl, isobutyl, tertiary butyl, n-pentyl and n-heptyl.

The compounds of formulae I, II and III wherein R is isopropyl

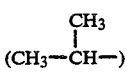

can be named bis[2,2,4-trimethyl-3-(2-methyl-1-oxopropoxy)pentyl]peroxydicarbonate, bis[3-(isobutyryloxy)-2,2,4-trimethylpentyl]peroxydicarbonate, and [3-(isobutyryloxy)-2,2,4-trimethylpentyl]-[2,2,4-trimethyl-3-(2-methyl-1-oxopropoxy)pentyl]-peroxydicarbonate respectively. Peroxydicarbonate compounds wherein R is other than isopropyl will be similarly named by substituting the appropriate radical names for the "isobutyryloxy" and "oxopropoxy" radicals in the aforesaid compound names.

The peroxydicarbonates of the graphic formulae I and II can be prepared from the chloroformate of the corresponding alcohols, e.g., 2,2,4-trimethyl-3-hydroxyl-1-isobutyryloxypentane and 2,2,4-trimethyl-3-isobutyryloxy-1-pentanol using known techniques for the manufacture of symmetrical peroxydicarbonates. The peroxydicarbonate of graphic formulae III can be prepared from a mixture, e.g., an equimolar mixture, of the haloformates, e.g., chloroformates, of the aforesaid alcohols. The mixture of chloroformates may be prepared by mixing the chloroformates or phosgenating a mixture of the alcohols. A mixture of the two chloroformates will upon reaction with hydrogen peroxide yield a peroxydicarbonate product comprising a mixture of the two symmetrical peroxydicarbonates, i.e., one from each of the chloroformates, and the unsymmetrical peroxydicarbonate, i.e., by reaction together of one mole of each of the chloroformates. The amount of each peroxydicarbonate produced from such a mixture of the chloroformates will be a function of the mole ratio of the two chloroformates and will follow a normal distribution. For example, an equimolar mixture of the primary and secondary ester chloroformates will (assuming equal reactivities produce a mixture of about 50% of the unsymmetrical peroxydicarbonate and about 25% each of the symmetrical peroxydicarbonate. Similarly, a mixture of primary to secondary ester chloroformates in a ratio of 2:1 (primary:secondary) will (assuming equal reactivities) produce a mixture of about 57% of the symmetrical peroxydicarbonate derived from the primary ester, about 14% of the symmetrical peroxydicarbonate derived from the secondary ester, and about 29% of the unsymmetrical peroxydicarbonate. The aforesaid preparative technique for peroxydicarbonates involves the careful reaction of the chloroformate(s) with aqueous sodium peroxide at low temperatures, usually less than 20° C., e.g., 0° C.–10° C., and is described in U.S. Pat. No. 2,370,588 and in Volume 72, page 1254 et seq (1950) of the Journal of the American Chemical Society.

The chloroformate of the precursor alcohol can be prepared by reaction of the alcohol with phosgene using well known phosgenation techniques. The precursor alcohols can be prepared by esterification of one hydroxy group of the alcohol, 2,2,4-trimethyl-1,3-pentanediol with $C_2$–$C_8$, preferably $C_2$–$C_6$, aliphatic monocarboxylic acids. Examples of the monocarboxylic acids that can be used include: acetic, propionic, butyric, isobutyric, valeric, caproic and caprylic acids. The partial esterification can be performed with the alcohol and carboxylic acid or with the alcohol (or sodium salt of the alcohol) with the acid halide, e.g. acid chloride, corresponding to the monocarboxylic acid. The aforesaid pentanediol is available commercially as is the mixture of the isobutyric acid monoesters of the aforesaid 1,3-pentanediol. This commercial mixture of esters is typically about 66 percent of the primary ester and about 34 percent of the secondary ester, i.e., the ratio of primary to secondary esters being about 2:1.

The peroxydicarbonates of the present invention may be used to polymerize ethylenically unsaturated monomers or mixtures thereof. The commercially important monomer vinyl chloride is particularly suitable. Vinyl chloride can be homopolymerized or copolymerized with up to about 15 percent of another ethylenically unsaturated monomer. Examples of monomers which are copolymerizable with vinyl chloride include vinylidene chloride, ethylene, propylene and vinyl acetate.

Polymerization of vinyl chloride is accomplished by contacting the vinyl chloride monomer or a mixture thereof with other monomers with an initiating amount of the peroxydicarbonate of the present invention under free-radical initiating conditions. Generally from about 0.003 to about 5, e.g., from 0.02 to 0.3, weight percent of the peroxydicarbonates of the present invention, based upon the total weight of monomer(s) polymerized, will be suitable for initiation of the polymerization. The precise amount of peroxydicarbonate used will vary with the monomers(s) to be polymerized and the polymerization temperatures. Typical levels of initiator required for such polymerizations are well known to those skilled in the art. The temperatures at which the polymerizable monomers can be polymerized will typically range from about 35° C. to about 75° C.

The peroxydicarbonates of the present invention can also be used to cure unsaturated polyester resins. Unsaturated polyester resins which can be cured with peroxydicarbonates are well known to those skilled in that art. Typically between about 0.05 and about 5, e.g., 0.2 to 2.5, parts by weight of the peroxydicarbonates will be added to 100 parts by weight of the unsaturated polyester resin composition. The resultant mixture is heated at a temperature of from about 20° C. to about 150° C., e.g., 50° C. to 100° C., whereby the resin is cured.

The peroxydicarbonates of the present invention may be used in combination with other normally liquid peroxydicarbonates and other commercially available organic peroxides such as peresters, diacyl peroxides and azo compounds. For example, the peroxydicarbonates of the present invention may be used in combination with, for example, diethyl peroxydicarbonate, diisopropyl peroxydicarbonate, di-n-propyl peroxydicarbonate, di-n-butyl peroxydicarbonate, disecondary butyl peroxydicarbonate, ditertiarybutyl peroxydicarbonate, di(2-ethylhexyl)peroxydicarbonate, diacetyl peroxide, dilauroyl peroxide, dibenzoyl peroxide, tertiarybutyl peroxypivalate, and azobisisobutyronitrile.

When used in combination with other normally liquid commercially available peroxydicarbonates, the mole ratio of the peroxydicarbonates of the present invention to that of the other normally liquid peroxydicarbonate may typically range from about 0.01:1 to about 10.1, e.g., 1:1.

The present invention is more particularly described in the following Examples which are intended as illustrative only since numerous modifications and variations therein will be apparent to those skilled in the art.

EXAMPLE I 108.2 (0.50 mole) of 2,2,4-trimethyl-1,3-pentanediol monoisobutyrate was added slowly to a reaction flask containing about 50 milliliters (ml) (0.73 mole) of phosgene cooled with an ice bath. The alcohol comprised a mixture of primary and secondary esters in a ratio of about 2:1 (primary:secondary). When the addition of the alcohol was completed, the ice bath was removed and the reaction mixture stirred for several hours. Excess phosgene was removed by passing nitrogen through the reactor for one hour. The phosgene-containing nitrogen gas stream removed from the reactor was forwarded to a packed column into the top of which was sprayed a solution of 15 weight percent sodium hydroxide which contained 0.8 weight percent pyridine. After degassing, 135.7 grams of a colorless liquid which was identified as the chloroformates of the alcohol by infrared (IR) and nuclear magnetic resonance (NMR) spectroscopy were recovered. The assay was determined to be 96.4 percent based on chloroformate chlorine analysis. The acidity level of the product was non-detectable.

EXAMPLE II 28.2 grams of the mixed chloroformates of Example I (without further purification) were mixed in a reactor with 3.8 grams of hydrogen peroxide in 10 grams of water and 60 grams of isopropanol. A homogenous mixture was obtained and to this mixture was added slowly 18.3 grams of a 25 weight percent sodium hydroxide solution while maintaining the mixture at 10° C. After completing the addition of the sodium hydroxide solution, the reaction mixture was stirred for 30 minutes.

The reaction mixture was washed three times with 100 mls of cold water. During each wash, about 10 milliliters of a saturated sodium chloride solution was added to enhance phase separation. The organic phase was collected in a small beaker chilled by an ice bath and dried with anhydrous magnesium sulfate. The organic phase was filtered to give a colorless liquid. Identification of the product was confirmed by IR and NMR spectroscopy. Iodometric titration of the product gave a percarbonate assay of 94.3 percent.

The half-life of the aforesaid peroxydicarbonate mixture at 50° C. was determined by maintaining separate aliquots of a 0.20M trichloroethylene solution of the peroxydicarbonate mixture in 5 milliliter ampoules in a constant temperature bath maintained at 50°±0.1° C. for various time intervals, and analyzing the amount of the peroxydicarbonate remaining in the ampoules after removal from the bath. The half-life was calculated to be 12.1 hours. The half-lives of diisopropyl peroxydicarbonate, disecondarybutyl peroxydicarbonate and di(2-ethylhexyl)peroxydicarbonate, as determined in the same manner, are 9.5, 9.0 and 9.2 hours respectively.

EXAMPLE III

The peroxydicarbonate mixture of Example II was used to polymerize vinyl acetate. The polymerization was performed in the following manner:

Vinyl acetate (50 grams), 0.05 mole percent of the peroxydicarbonate initiator, basis the vinyl acetate monomer, and 100 grams of a 0.1 weight percent aqueous solution of Methocel E-50 suspending agent were charged to 28 ounce polymerization bottles, which were chilled by an ice bath. The atmosphere inside the bottles was removed by passing argon through the mixture for three minutes. The bottles were then capped, sealed and secured in safety cages. The cages and bottles were placed in a constant temperature water bath maintained at 40° C. and the bottles tumbled at a rate of 30 revolutions per minutes for four hours.

One bottle was removed from the water bath at the end of each hour. This bottle was opened immediately and the contents poured into a two liter beaker containing about 1500 milliliters of hot water (about 50°-60° C.). The resulting aqueous suspension was then heated to boiling to remove the unreacted vinyl acetate monomer. The precipitated polymer was collected, washed with distilled water and dried in a vacuum oven at room temperature for at least 24 hours.

The intrinsic viscosity (in toluene, 25° C.) of each dried product was determined and the molecular weight of each polymer product was calculated from the intrinsic viscosity according to the Mark-Houwink equation. Results obtained are tabulated in Table I. The results are also compared to typical results for the suspension polymerization of vinyl acetate at 40° C. with 0.05 mole percent of di(secondary butyl)peroxydicarbonate and di(2-ethylhexyl)peroxydicarbonate.

TABLE I

| Suspension Polymerization of Vinyl Acetate at 40° C. | | | | | |
|---|---|---|---|---|---|
| Peroxy-dicarbonate | Amt. (Mole %) | Poly (vinyl acetate) % Conversion (Molecular Weight, $10^5$) | | | |
| | | 1 hr. | 2 hrs. | 3 hrs. | 4 hrs. |
| 1. Example 2. | 0.05 | 15 (2.1) | 39 (2.8) | 65 (3.0) | 80 (3.9) |
| 2. SBP[a]. | 0.05 | 28 (4.9) | 67 (6.7) | 82 (7.7) | 82 (7.9) |
| 3. EHP[b]. | 0.05 | 26 (3.3) | 57 (4.3) | 81 (5.2) | 85 (5.3) |

[a]disecondarybutyl peroxydicarbonate
[b]di(2-ethylhexyl)peroxydicarbonate

The data of Table I show that the peroxydicarbonate mixture of Example II was effective as an initiator for vinyl acetate—80 percent conversion of the monomer being obtained after 4 hours compared to 82 and 85 percent conversion for other commercially available peroxydicarbonate. The data also shows that the molecular weight of the polymer obtained with the peroxydicarbonate mixture of Example II was less than that for the commercially available peroxydicarbonates, thereby providing a different poly(vinyl acetate). It is expected that similar results will be obtained with other peroxydicarbonates of the present invention for vinyl acetate and other ethylenically unsaturated monomers such as vinyl chloride.

Although the present invention has been described with reference to specific details of certain embodiments thereof, it is not intended that such details be regarded as limitations upon the scope of the invention except as and to the extent that they are included in the accompanying claims.

What is claimed is:

1. Peroxydicarbonates represented by the graphic formulae:

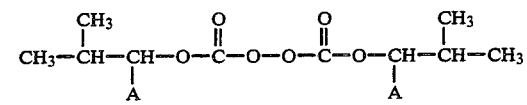

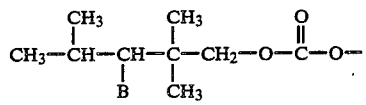

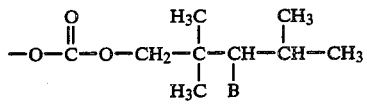

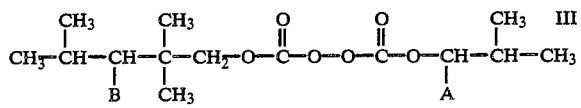

wherein A is the radical

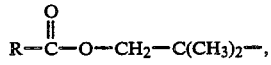

B is the radical

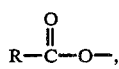

and R is a $C_1$–$C_7$ alkyl radical.

2. The peroxydicarbonate of claim 1 wherein R is a $C_1$–$C_5$ alkyl radical.

3. Bis[2,2,4-trimethyl-3-(2-methyl-1-oxopropoxy)pentyl]peroxydicarbonate.

4. Bis[3-(isobutyryloxy)-2,2,4-trimethylpentyl]peroxydicarbonate.

5. [3-isobutyryloxy)-2,2,4-trimethylpentyl]-[2,2,4-trimethyl-3-(2-methyl-1-oxoproxy)pentyl]peroxydicarbonate.

6. A mixture of peroxydicarbonates represented by the graphic formulae

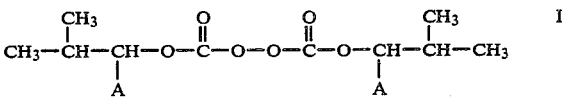

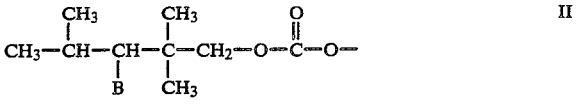

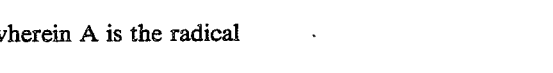

wherein A is the radical

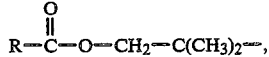

B is the radical $$R-\overset{O}{\underset{\|}{C}}-O-,$$

and R is a $C_1$–$C_7$ alkyl radical, said peroxydicarbonate mixture having been prepared by the reaction of hydrogen peroxide with the haloformates of the mono ($C_2$–$C_8$) carboxylic acid esters of 2,2,4-trimethyl-1,3-pentanediol.

7. The peroxydicarbonate mixture of claim 6 wherein R is isopropyl, and the ratio of the primary ester to the secondary ester is about 2:1.

* * * * *